United States Patent [19]

Skeie et al.

[11] Patent Number: 5,180,392
[45] Date of Patent: Jan. 19, 1993

[54] ANASTOMOTIC DEVICE

[76] Inventors: Einar Skeie, Dyrehavegardsvej 45, DK-2800 Lyngby; Daniel Bar-Shalom, Rypevaenget 213, DK-2980 Kokkedal, both of Denmark

[21] Appl. No.: 614,690

[22] Filed: Nov. 15, 1990

Related U.S. Application Data

[63] Continuation of Ser. No. 305,529, Feb. 1, 1989, abandoned.

[30] Foreign Application Priority Data

Feb. 1, 1988 [DK] Denmark .................. 505/88

[51] Int. Cl.$^5$ ............................. A61F 2/04
[52] U.S. Cl. ................................. 623/11; 606/155
[58] Field of Search ............ 623/11, 12; 606/153, 606/155, 156

[56] References Cited

U.S. PATENT DOCUMENTS

| | | | |
|---|---|---|---|
| 1,470,707 | 10/1923 | Bates | 128/334 R |
| 2,428,918 | 10/1947 | Miller | |
| 3,155,095 | 11/1964 | Brown | 128/334 C |
| 3,620,218 | 11/1971 | Schmitt | 606/155 |
| 3,683,926 | 8/1972 | Suzuki | 623/66 |
| 3,883,901 | 5/1975 | Coquard et al. | 623/1 |
| 3,938,528 | 2/1976 | Bucalo | |
| 4,182,339 | 1/1980 | Hardy, Jr. | |
| 4,483,339 | 11/1984 | Gillis | |
| 4,552,148 | 11/1985 | Hardy, Jr. et al. | |
| 4,587,969 | 5/1986 | Gillis | |
| 4,743,258 | 5/1988 | Ikada et al. | 623/11 |
| 4,770,176 | 9/1988 | McGreevy et al. | 128/334 R |

FOREIGN PATENT DOCUMENTS

| | | |
|---|---|---|
| 0070923 | 2/1983 | European Pat. Off. |
| 0119848 | 9/1984 | European Pat. Off. |
| 2034413 | 1/1972 | Fed. Rep. of Germany |
| 2546283 | 5/1976 | Fed. Rep. of Germany |
| 2164562 | 3/1986 | United Kingdom |

Primary Examiner—David Isabella
Attorney, Agent, or Firm—Birch, Stewart, Kolasch & Birch

[57] ABSTRACT

A prosthesis for use in joining hollow, e.g. tubular, organ parts or systems, said prosthesis comprising a fragmentable body defining outer organ-supporting surface parts thereon adapted to be arranged in abutting relationship with inner surface parts of the organs to be joined, said body having a compressive strength sufficiently low to allow fragmentation of the body by application of a pressure to the outer surface of the tubular organs subsequently to the joining of the same, said pressure being below a pressure causing any substantial lesion of the tissue of the tubular organ parts. The material of the prosthesis is preferably one or more degradable and/or erodable and/or water-soluble, essentially non-toxic materials which are solid at a temperature of 40° C. or higher, in particular 60° C. or higher, the material preferably being a polyether, more preferably a polyglycol, in particular polyethylene glycol such as polyethylene glycol with an average molecular weight of from 10,000 to 35,000, especially about 20,000.

As shown in FIG. 3, the prosthesis (1) may have tapered outer ends (3) as well as an intermediary portion (4) between the organ-supporting parts and having a smaller diameter. In another embodiment as shown in FIG. 9 or FIG. 13, the end portions may consist of longitudinally and inwardly radially extending fins (11) to give the prosthesis tapering end portions. In a further embodiment, the prosthesis may be a section of tubing with ends cut at an oblique or right angle.

22 Claims, 2 Drawing Sheets

Fig. 1
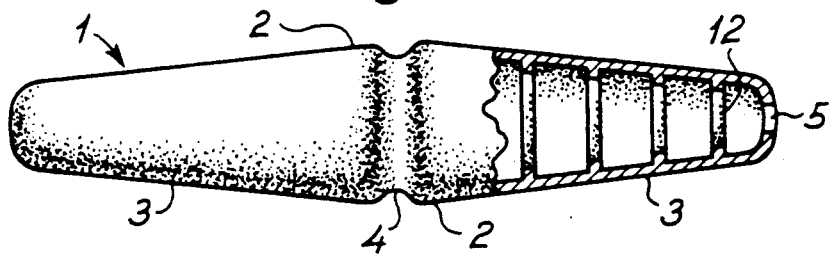
Fig. 2 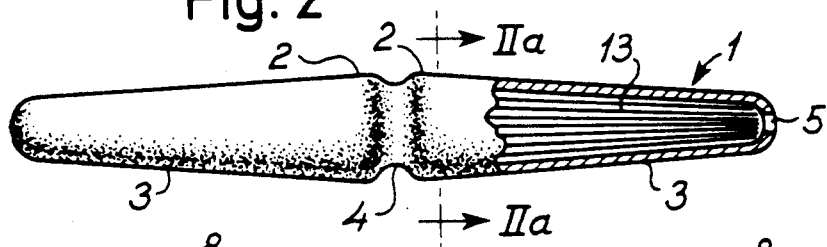 Fig. 2a 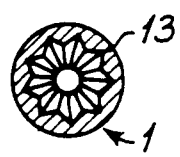
Fig. 3 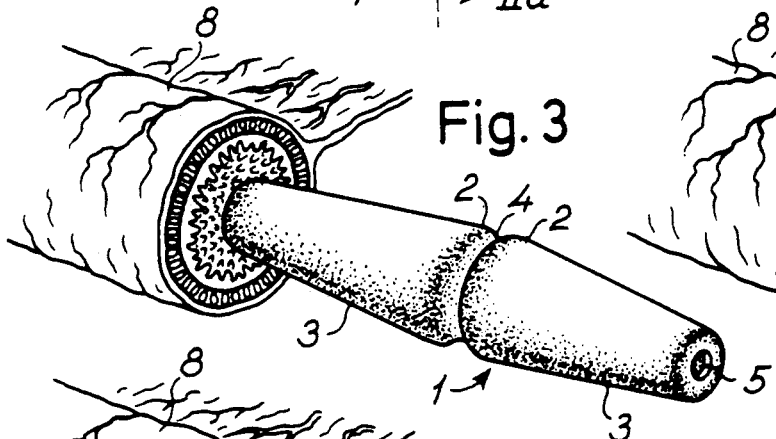 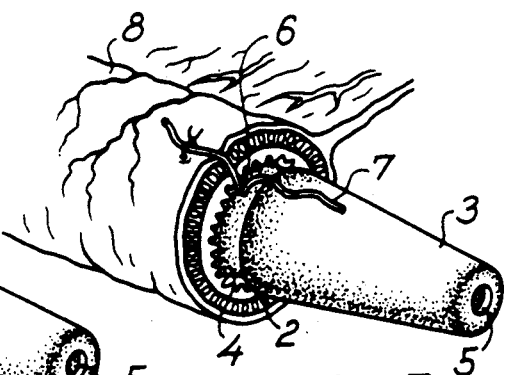 Fig. 7

Fig. 5 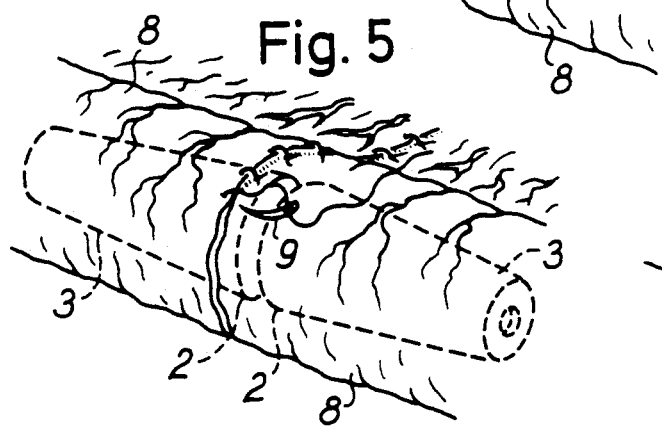 Fig. 6 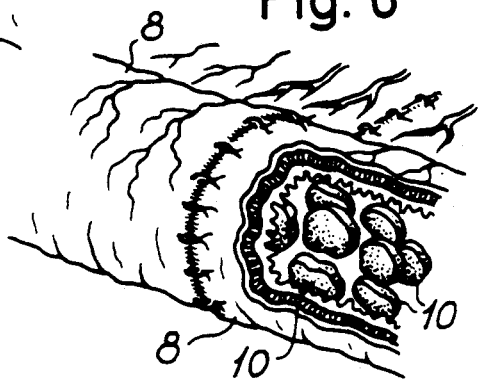

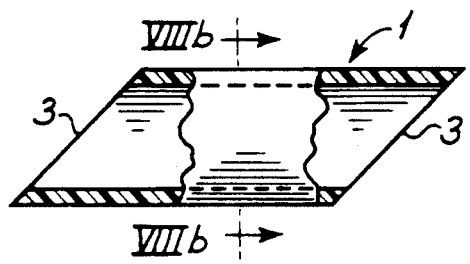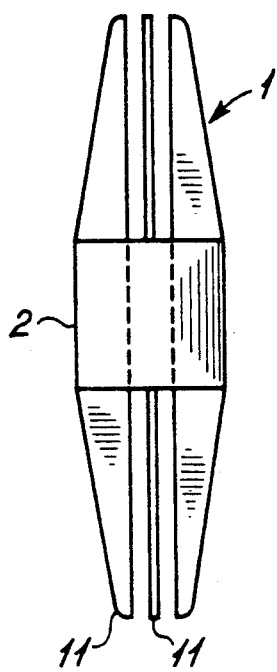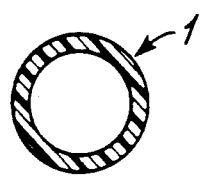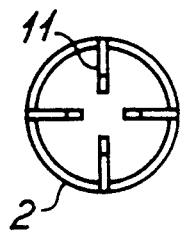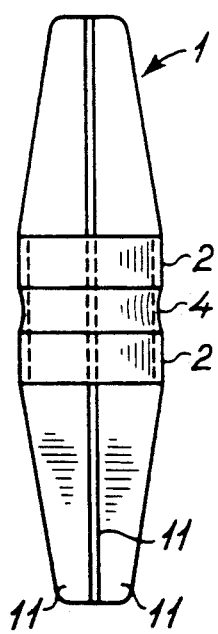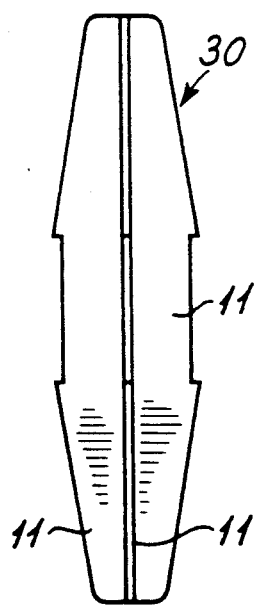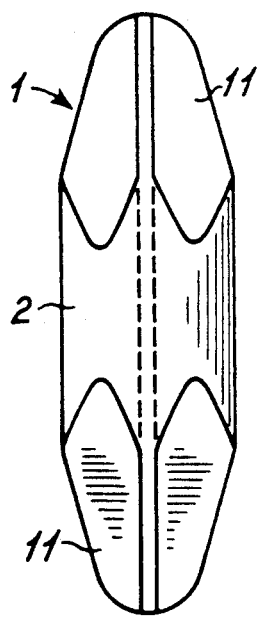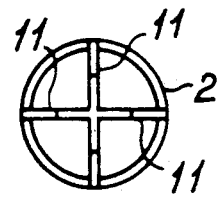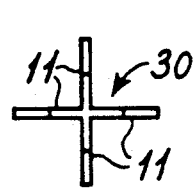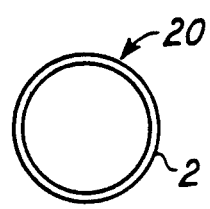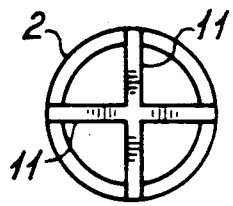

ANASTOMOTIC DEVICE

This is a continuation of application Ser. No. 305,529, filed Feb. 1, 1989, now abandoned.

BACKGROUND OF THE INVENTION

1. Field of the Invention

The present invention relates to a prosthesis for use in joining hollow, e.g. tubular, organ parts or systems.

2. Description of the Prior Art

When joining hollow or tubular organ parts or systems by anastomosis (i.e. create a communication between formerly separate structures), e.g. intestines (large as well as small) ventricle, duodenum and esophagus, problems are often encountered due to the fact that the organs are soft and flaccid and because there is no hard support against which to carry out the suturing. For example, when joining the intestines, the lack of support often leads to an anastomosis that subsequently leaks or heals with a constriction in the intestine, thereby forming a partial obstruction of the intestinal pathway. Thus, many intestinal anastomoses require re-operation in order to alleviate the constriction.

On the other hand, any supporting body inserted into the tubular organ cannot be immediately removed when the anastomosis is finished. Various attempts have been made to provide support prosthesis that are slowly broken down, e.g. by gastric juices. However, the long break-down time of such prostheses can cause temporary partial or complete blockage of the intestine.

As a consequence of the above, surgical prosthesis for joining hollow or tubular organ parts or systems, in particular intestines, have not been used extensively. Consequently, there is a need for prosthesis for use in suturing and anastomosing tubular organ parts which are somehow easily removable from the operation site once the anastomosis is finished.

SUMMARY OF THE INVENTION

The present invention solves the above-described problems by providing a prosthesis which can be crushed or fragmented after the anastomosis. Thus, the invention concerns a prosthesis for use in joining by anastomosis hollow, e.g. tubular, organ parts or systems, said prosthesis comprising a fragmentable body defining outer organ-supporting surface parts thereon adapted to be arranged in abutting relationship with inner surface parts of the organs to be joined, said body having a compressive strength sufficiently low to allow fragmentation of the body by application of a pressure to the outer surface of the tubular organs subsequent to the anastomosing of the same, said pressure being below a pressure causing any substantial lesion of the tissue of the tubular organ parts.

DETAILED DESCRIPTION OF THE INVENTION

Figure 4:
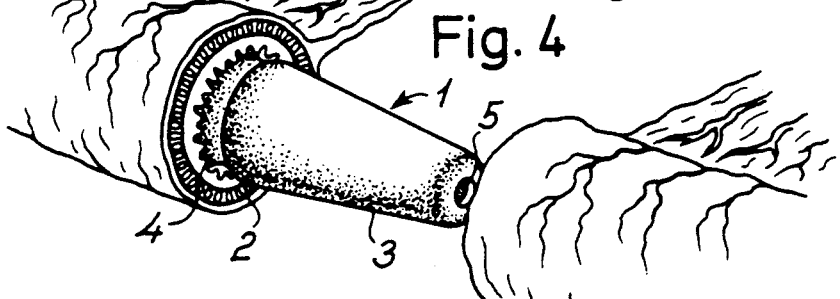

The compressive strength of the body will, naturally, depend very much on the properties of the tubular organ parts that are to be joined by anastomosis. Thus, some types of organs, e.g. esophagus, are more susceptible to lesions and hemorrage, whereas certain parts of other organs such as the intestines may be less prone to lesions. Consequently, it is clear that the compressive strength of the prosthesis can vary within very wide limits. Furthermore, it is difficult to express the compressive strength in mechanical terms since it will also depend on the exact way in which the pressure is applied to the prosthesis. As an example, it may be mentioned that a specimen of an experimental prosthesis which had been used successfully for anastomosing a small intestine was tested by subjecting it to compression by means of an inflatable blood pressure cuff. In the experiment, the prosthesis broke at a cuff pressure of 280 mm Hg. Another specimen of the same prosthesis was crushed by pressing it with the fingers of one hand, and it was estimated that a pressure of 300–400 g had been exerted on the breaking point. The upper limit of the breaking strength of the prosthesis can easily be determined by those skilled in the art, e.g. by conducting tests on fresh tissue samples to determine the pressures at which substantial lesion occurs.

Another test method which fairly closely simulates use conditions, i.e. breaking the prosthesis by pressing it between the thumb and four opposing fingers, is the test method described in example 2 where the prosthesis is pressed between a planar surface and a cylindrical, planar-faced mandrel with a diameter of 24 mm (simulating a finger), the mandrel being pressed with a displacement rate of 20 mm/minute. When tested under these conditions and at room temperature, it is preferred that the prosthesis of the invention has a compressive strength in the range from 20 to 100N, in particular from 30 to 80N, especially from 40 to 70N such as from 50 to 60N.

Thus, the prosthesis of the invention is advantageous in that it can be crushed into small fragments after the anastomosis operation whereupon the fragments can be removed by natural processes such as peristaltis. The prosthesis of the invention is mainly suitable for use in "open" organ systems such as the digestive tract where the fragments can be excreted at a later time.

A significant advantage that has been established when using a prosthesis of the invention for joining intestines is that the surgeon on the one hand is able to effectively remove the prosthesis subsequent to the anastomosis operation and secondly is enabled to employ a suturing technique which only very rarely is employed in such contexts. During a normal anastomosis operation, without the use of a prosthesis, the surgeon will, during an anastomosis of the small intestine in a human adult, typically first make approximately 17 stitches where the needle is passed through the entire intestinal wall (that is through the outer layer, the muscular layer and the mucosa) into the lumen of the two organ halves, thereby joining the two halves together. The stitches are placed equidistantly along the peripheri of the two organ sections. The stitches are made separately as interrupted stitches, each being tied with a knot. Following this, the surgeon will then make another set of approximately 17 stitches in between the first set, the second set of stitches being characteristic in that the needle is only hooked through the outher and muscular layer of the intestines, some 3 mm from the edges of the sectioned intestine, and these stitches are then used to pull together very tightly the two organ halves so that the approximately 3 mm of "superfluous" intestine projects into the lumen of the intestine. Also these second stitches are made separately and interrupted by typing separate knots. All in all, a total of approximately 35 stitches is necessary for carrying out a typical small intestine anastomosis, and it would be highly desirable to be able to reduce the number of stitches since these cause a certain amount of strain on the intestinal tissue. In particular, it would be desirable if it was possible to reduce the number of stitches penetrating into the lumen of the intestine, thereby reducing the risk of inflammation due to seepage of digestive juices along the surgical thread going from the lumen and out through the muscular layers of the intestine.

Using the prosthesis of the invention, the surgeon is able to employ the so-called continuous single-layer suturing technique whereby connected stitches are made, i.e. not interrupted stitches, by hooking the needle through only the muscular layers (i.e. not through to the lumen) on alternate sides of the anastomosis site and then finally pulling the two organ halves together by tightening the continuous thread. In this manner, the number of stitches in a typical small intestine anastomosis could be reduced by some 30% which is highly desirable since it places less of a strain on the organ tissues.

It will be evident that the fragments from the prosthesis of the invention are much easier for the body to get rid of than an entire, albeit degradable, prosthesis according to the prior art. However, according to the present invention it is also preferred that the prosthesis is prepared from one or more degradable and/or erodable and/or water-soluble, essentially non-toxic materials in order to facilitate removal and/or degradation of the fragments left after the prosthesis has been crushed. In order to be able to withstand body temperatures as well as local higher temperatures that may arise during operations under strong illumination, it is preferred that the material or materials from which the prosthesis is made, are solid at a temperature of 40° C. or higher, more preferably 50° C. or higher, in particular 60° C. or higher.

The prosthesis may be prepared from one or more of the following materials such as fats, esters, waxes, fatty alcohols, ethers, natural polymers, synthetic polymers, and others. Examples of these classes of materials are hard paraffin, beeswax, ceresin, higher fatty alcohols such as cetyl, stearyl, cetostearyl alcohol and the like, cholesterol, japan wax, kokkum butter, lard, microcrystalline wax, fractionated palm kernel oil, spermaceti, cetyl esters wax, squalane, wool alcohols, wool fat, carnauba wax, polyglycols, theobroma oil, chocolate, macrogol ethers, glycerol ethers, glycol ethers, poloxamers, and others.

In a preferred embodiment, the prosthesis may be prepared from a material that forms a viscous gel on the surface when brought into contact with water or body fluids. This swelling or partial dissolution of the surface layer is useful to the surgeon carrying out the anastomosis in that the organ parts to be joined will stick or adhere to the organ supporting surface parts of the prosthesis of the invention, thereby facilitating the operation by ensuring that the prosthesis stays in its proper location during the anastomosis operation. Among the materials mentioned above, examples of such materials forming a viscous gel on the surface following contact with water or body fluids are fatty alcohols, spermaceti, wool alcohols, wool fat, polyglycols, theobroma oil, chocolate, macrogol ethers, glycerol ethers, glycol ethers and poloxamers. Specific examples of some of these types and materials are given above.

A particularly preferred class of materials are polyethers such as polyglycols, in particular polyethylene glycol. The polethylene glycol may, in a preferred embodiment, have an average molecular weight in the range from 10,000 to 35,000, in particular from 15,000 to 30,000, especially about 20,000. Such polyglycols have exhibited particularly useful properties with respect to forming a sticky, viscous gel on the surface of a prosthesis made therefrom following contact with water or body fluids.

For the purpose of exerting an beneficial effect on the healing of the anastomosis or removal of the prosthesis fragments, the prosthesis of the invention may incorporate one or more pharmaceutically active substances such as antibiotics, antiseptics, locally active substances, cytostatics, local anaesthetics, healing accelerators, purgatives, or bulk or osmotic laxatives; or substances that make the prosthesis hydrophobic (e.g. polyethylene glycol monostearate), as well as dissolution accelerators (e.g. low molecular polyglycols, salt, potato starch, or methyl cellulose). The above-mentioned substances may be incorporated in the prosthesis in several ways such as mixed with or embedded in the material in which the prosthesis body is manufactured; or they may be deposited on the surfaces of the prosthesis; or, if the prosthesis is of the closed shell type, they may be placed inside the shell as e.g. a powder for release upon fragmentation of the prosthesis subsequently to the operation.

With respect to the physical shape of the prosthesis of the invention, the prosthesis may have a substantially circular cross-section although this does not exclude the possibility of using prostheses with e.g. oval or elliptical cross-sections.

Depending on the use, the ratio between the length and the largest diameter of the prosthesis of the invention may normally be in the range of from 1.5:1 to 10:1, preferably from 2:1 to 7:1.

In one embodiment of the prosthesis of the invention, the body of the prosthesis comprises end portions, the organ-supporting surface parts and a narrowed intermediary portion therebetween. The advantage of this embodiment is that the narrowed intermediary portion facilitates the suturing operation since surgical suturing needles are generally curved whereby the narrowed intermediary portion will make it less probable that the surgeon will hit the prosthesis with the needle.

In another preferred aspect, the end portions of the prosthesis of the invention have rounded and/or tapered outer ends. This facilitates insertion of the prosthesis into the tubular organ parts prior to suturing.

The body of the prosthesis may have varying inner structures. Thus, the body could conceivably consist of a friable foam-like structure that could be fragmented. In a preferred embodiment, the body of the prosthesis defines an inner cavity. In other words, the prosthesis has a shell-like structure. In certain applications, such a body defining an inner cavity may advantageously have closed ends, e.g. for reasons of structural strength. In other applications it may be advantageous that the ends of the prosthesis body are open, e.g. in anastomosing intestines where it may be advantageous not to block the intestine during the operation, but instead to have free passage through the prosthesis during the operation. It is also possible to have outer surfaces with an open structure such as a perforated or net-like surface.

In order to eliminate the danger of the prosthesis slipping inside the tubular organ along the organ's longitudinal axis during the operation, the prosthesis may be provided with at least one e.g. thread-like fixation means having one end connected to the intermediary portion of the body for temporarily fixing the organ parts to the prosthesis. The thread-like fixation means could consist of e.g. a short length of suturing thread having one fixed to the surface of the prosthesis, e.g. in the narrowed intermediary portion mentioned above. The prosthesis could be provided with for example three pairs of short pieces of suturing thread, the pairs of thread being arranged equidistantly around the cross-sectional circular periphery of the prosthesis such as 120° from one another. Such fixation means would be used in that the surgeon, having inserted the two halves of the prosthesis into each of the two organ parts to be joined, initially fixes, e.g. by suturing, each organ part to the prosthesis prior to carrying out the actual detailed anastomosis of the two organ parts. In this manner, the prosthesis will be fixed in relation to the anastomosis site and will not slip in relation thereto during the suturing operation.

The prosthesis of the invention may be manufactured by a number of well-known techniques used in the manufacture of shaped objects. Thus, the prosthesis of the invention may be manufactured by injection moulding, centrifugal moulding, extrusion, rollering, calandering, welding, etc. Since the prosthesis of the invention must ultimately be presented in sterile form, it is preferable to use a manufacturing technique necessitating as few as possible operations.

Thus, injection moulding is a particularly preferred method, provided that the shape of the prosthesis allows the use of injection moulding. Injection moulding is particularly useful if the material from which the prosthesis is made is thermoplastic, e.g. polyethylene glycol.

The prosthesis of the invention will typically be presented to the user in a sterile package, and the prosthesis will therefore need to be sterilized after having been shaped. The prosthesis could be sterilized by means of a gaseous or liquid sterilizing agent such as ethylene oxide, but since such sterilization methods only sterilize the surface of the prosthesis, and the prosthesis is broken into smaller pieces after the anastomosis operation, it is preferred to use a sterilization method which ensures that the prosthesis is sterilized throughout, i.e. that also microorganisms embedded in the material forming the walls and other parts of the prosthesis are killed. Consequently, a preferred sterilization method is sterilization by radiation, e.g. irradiation with β-particles or irradiation with γ-rays, in particular β-particles, preferably subsequent to packaging.

The invention further concerns a method for joining hollow, e.g. tubular organ parts or systems, said method comprising 1) inserting a prosthesis of the invention into and between the two organ parts to be joined;

2) joining the organ parts by anastomosis; and 3) fragmenting the prosthesis by application of a pressure to the outer surface of the organ part.

In the method of the invention, the bond may be made by any means such as suturing, gluing, stapling or combinations thereof.

The prosthesis of the invention can be used for the anastomosis of a number of organs, such as in the gastro-intestinal tract (e.g. esophagus, ventricle, duodenum, small intestine, large intestine, rectum, bile canal, etc.) and the urogenital system (e.g. ureter, urethra, bladder, etc.).

With the large variation in diameters of the above-mentioned organs, it is evident that the prosthesis of the invention can be manufactured in a number of different sizes according to the particular organ or organs which are to be anastomosed. Thus, the prosthesis could e.g. be adapted to aid in anastomosing organs of differing sizes, such as by anastomosis of the large and small intestine, where, previously, it was common to conduct so-called "side-by-side" anastomosis. By using a suitably adapted prosthesis of the invention, it may be possible to stretch the smaller organ (in this case, the small intestine) to better suit the diameter of the large organ. In order to facilitate establishing what size of the prosthesis should be used, the surgeon could be provided with a purpose-made measuring gauge or mandrel, typically a conical gauge which, prior to the anastomosis, is inserted into the hollow organ or organs to be anastomosed after which the surgeon can directly on the gauge read off the proper size of prosthesis.

The invention will now be further explained with reference to the drawing in which FIGS. 1, 2 and 8–13 show embodiments of the prosthesis of the invention, and FIGS. 3–7 illustrate the use and function of the prosthesis according to the invention.

In the Figures like numerals designate like objects.

FIG. 1 is a partly broken away view of the prosthesis according to the invention designated 1 in its entirety. The prosthesis is a tubular body, the largest diameter parts of which constitute organ-supporting surface parts 2. The end portions 3 of the prosthesis have tapered outer ends to facilitate the introduction of the prosthesis into the tubular organ part prior to the suturing. The intermediary portion 4 between the organ-supporting parts has a smaller diameter and thus provides a "work area" for the suturing needle and substantially reduces the risk that the needle would hit the prosthesis during the suturing. The prosthesis of FIG. 1 is shown as a body defining an inner cavity, that is, a hollow body. In the embodiment shown, the wall of the prosthesis is reinforced with circular ribs 12. Such reinforcement may be of interest e.g. for prostheses for larger organs where a certain reinforcement of the walls is desirable to avoid premature fracturing of the prosthesis. The prosthesis is open at both ends as shown by 5; this may facilitate passage of organ contents such as intestine contents through the prosthesis. Depending on the intended use of the prosthesis, its largest diameter may be between about 5 mm and about 50 mm, the smaller diameters being adapted e.g. for small intestines of infants and the largest diameters being adapted e.g. for the large intestines of adults.

FIG. 2 is a partly broken away view of a similar prosthesis as shown in FIG. 1, this time, however, with substantially axially extending grooves 13 which, contrary to the ribs 12 in FIG. 1, exert a notch effect to facilitate the fracturing of the prosthesis. This may be of interest for small diameter prostheses. FIG. 2a shows a cross-section of the prosthesis in FIG. 2. However, in many cases neither the ribs of FIG. 1 nor the notches of FIG. 2 will be needed, provided the material and the dimensions of the prosthesis walls are suitably adapted to the circumstances under which they are to be used as support and later on fractured.

FIGS. 3–7 schematically show the use of a prosthesis of the invention, in the present case a prosthesis as shown in FIG. 1 or FIG. 2. FIGS. 3 and 4 demonstrate how the prosthesis 1 is inserted into the two ends of a tubular organ 8 that are to be anastomosed. In FIG. 5 it can be seen how the prosthesis 1, which is shown as a broken outline, serves as the support for the anastomosis of the tubular organs by means of a surgical needle and thread 9. Subsequently to the anastomosis, the prosthesis of the invention is, as already outlined above, fractured into a plurality of pieces 10 shown in the partly broken away view in FIG. 6. FIG. 7 shows a variation of the prosthesis of the invention, the prosthesis further being equipped with embedded fixation threads 7 which are connected to the prosthesis at the point 6 in the intermediary portion 4.

FIGS. 8a and 8b are longitudinal and transversal views, respectively, of another prosthesis of the invention. In this type of prosthesis, the prosthesis 1 merely consists of an obliquely cut piece of circular tube. Such a prosthesis has the advantage of being very easy to manufacture, e.g. by injection moulding or, in particular, extrusion. The obliquely cut ends aid in the insertion of the prosthesis into the tubular organ since the organ can be slowly pulled over the ends of the prosthesis under gradual expansion. However, for use with some organs, the prosthesis may well be a simple piece of circular tube cut at right angles, optionally with bevelled or rounded (by melting) edges to avoid damaging the organ during the insertion due to sharp edges.

FIG. 9 is a side view of yet another prosthesis of the invention having cylindrical organ-supporting surface parts 2 in the middle, whereas the remainder of the body of the prosthesis consists of longitudinally and inwardly radially extending fins 11 which have been cut at an angle to, in effect, give the prosthesis tapering end portions. FIG. 9a is a cross-sectional view of the prosthesis of FIG. 9. In the prosthesis in FIGS. 9 and 9a, the number of longitudinally and inwardly radially extending fins 11 is four, but it is equally possible to have a prosthesis of this type in which the number of fins is three or five or more, set at equal or different angles to one another. Thus, with three fins these may be set at 120° from one another. The prosthesis in FIGS. 9 and 9a has the advantage that it can be manufactured in one operation by injection moulding whereas e.g. a prosthesis as shown in FIG. 1 or FIG. 2, will normally have to be manufactured by e.g. centrifugal moulding.

FIGS. 10, 10a, 11, 11a, 12 and 12a are side views and cross-sectional views of a variation of the prosthesis shown in FIGS. 9 and 9a. This prosthesis has also longitudinally and radially extending fins 11, but in this embodiment, the fins are cast as a separate object as shown in FIG. 11. FIG. 11a shows the cruciform cross-section of the fin body designated 30 in its entirety. FIG. 12 shows a tubular sleeve designated 20 in its entirety, having organ-supporting surface parts 2 and an intermediary portion 4 with a smaller diameter. FIG. 12a is a cross-sectional view of the sleeve in FIG. 12 and shows its circular cross-section. FIGS. 10 and 10a are a side view and a cross-sectional view, respectively, of the prosthesis assembled from the fin body 30 and the sleeve 20. Also in this case, the number of fins shown is four, but, as mentioned previously, the number of fins may in this case also be three, five or more. Such a configuration would have the advantage that no matter at what two diametrically opposed points the pressure was applied radially to the prosthesis, the prosthesis would always have practically the same breaking strength. In the case of the fin body 30 having a cruciform cross-section as shown in FIG. 11a, it would most likely require greater pressure to crush the prosthesis if the pressure was applied in line with the radial extension direction of the fins compared to the case that the pressure was applied to points in the space between the fins.

FIGS. 13 and 13a show a side view and an end view, respectively, of a variation of the prosthesis shown in FIGS. 9/9a or 10/12a. In this embodiment, the organ-supporting surface parts 2 have been partly extended longitudinally around the fins 11. This has the advantage that when the prosthesis is inserted into the tubular organ part and expands the organ to some extent, the expanded organ does not, as in e.g. the prosthesis shown in FIG. 9, present a square cross-section which then has to be "lifted" to be supported on the cylindrical organ-supporting surface parts in the middle section of the prosthesis. With the prosthesis shown in FIG. 13, the tubular organ will gradually assume a circular cross-section as it is pushed further and further along the fins 11 towards the central part of the prosthesis. Thus, the prosthesis shown in FIG. 13 has the advantages inherent in a prosthesis such as the one shown in FIG. 1, but is at the same time of a structure that can be manufactured by simple injection moulding. Although the number of fins shown in FIGS. 13 and 13a also in this case is four, the number of fins may, as described previously, also be three, five or more and distributed in the manner described above.

The invention is further illustrated by the following non-limiting examples:

EXAMPLE 1

A prototype prosthesis of the invention was prepared in the following manner: An ordinary cylindrical laboratory test tube with a diameter of 15 mm and a hemispherical bottom was coated with a thin layer of silicone grease. Thereafter, the test tube was dipped into molten polyethylene glycol (Polyglycol 20,000 from Hoechst, West Germany) kept at a temperature of 100° C. The test tube was withdrawn from the molten polyethylene glycol, and the deposited layer was allowed to crystallize. Thereafter, the solidified sheath of polyethylene glycol was carefully slid off the test tube. The sheath was cut off at ca. 50 mm from the rounded end. From another sheath prepared in the same manner, the extreme 20 mm of the sheath (including the closed end) was cut off and joined to the first open-ended tube by careful warm-welding. The result was a cylindrical closed shell with hemispherical ends and a length of 70 mm and a diameter of ca. 15 mm. The wall thickness of the shell was 0.5–1.0 mm.

A prosthesis prepared in the above manner was tried out in a test operation conducted on a recently deceased human being. After opening of the abdominal cavity, a section of the small intestine was cut, the cut continuing approximately 50 mm up into the mesenterium. Thereafter, the prosthesis was inserted into the ends of the intestine, and the two ends were then joined by suturing in the normal manner. The anastomosis was easy to carry out and was finished in approximately 10 minutes. Following the anastomosis, the prosthesis was crushed by applying pressure on the outside of the anastomosed intestine by means of the thumb and two first fingers which caused collapse of the prosthesis. As a surgical aid, the prosthesis performed excellently.

In order to investigate the fragmentation process, the intestine was, following the anastomosis, opened longitudinally which revealed that the prosthesis had broken into a large number of small pieces up to a size of approximately 10 mm in the largest dimension. The edges of the pieces were not sharp due to the mechanical properties of the polyethylene glycol. It was estimated that excretion of such fragments, quite apart from the fact that polyethylene glycol is soluble in water, would not present any problems. Furthermore, close examination of the inner epithelium of the intestine showed that the mucous membrane had not suffered any damage as a result of the crushing in spite of the fact that the mucous membrane of a cadaver is considerably more sensitive to lesions caused by pressure than the mucous membranes of a living person. This indicates that the prosthesis would not have caused any damage whatsoever when used in a normal intestinal anastomosis.

In order to quantify the breaking strength of the prosthesis, another prosthesis prepared in the same manner was tested by wrapping a blood pressure cuff around it and inflating the cuff until the prosthesis was crushed. The result was that the prosthesis broke at a over-pressure of 280 mm Hg in the cuff (measured on the connected mercury column). Also, a prosthesis was broken manually by pressing it between the thumb and four opposed fingers, and it was estimated that a pressure of approximately 300-400 grams was exerted at the point where the prosthesis broke.

EXAMPLE 2

Surgical prostheses were made from polyethylene glycol with a molecular weight of 20,000, (Polyglycol 20000 from Hoechst, West Germany; Pharmaceutical Quality). The prosthesis were cylindrical tube sections having an outer diameter of 22 mm, a wall thickness of 2 mm and a length of 68 mm.

The prostheses were manufactured by injection moulding on a Klöchner Ferromatic injection moulding machine which had been modified in order to operate with polyethylene glycol. The modification consisted of replacing the normal knock-out pins with a cylindrical or tubular knock-out member due to the low mechanical strength of the polyethylene glycol. By using the cylindrical or tubular member as the knock-out pin, breakage of the fragile prosthesis was prevented due to the larger support area. Furthermore, the polyethylene glycol was supplied in the form of flakes which, due to their inferior flowability, did not introduce well into the melting chamber of the injection moulding machine. It was necessary to assist manually the introduction of the flakes into the melting chamber. The injection moulding machine was run with a nozzle temperature of 65° C.

Surgical prostheses of this type were tested for compressive strength both untreated and following immersion into a simulated gastric juice solution and following irradiation and combination thereof. The measurement of compressive strength was carried out by placing the prosthesis on a planar surface and pressing on the middle of the cylindrical side until fracture. The strength testing was carried out by pressing a cylindrical, planar-faced mandrel with a diameter of 24 mm against the prosthesis with a displacement rate of 20 mm/minute. The mandrel was connected with a strain gauge and the parameters measured were the compressive strength (at fracture), the module and the linear displacement at the time of fracture. The measurement was made at room temperature.

The measurements were carried out on untreated samples as well as samples immersed for 5, 10 and 20 minutes at 37° C. and under slight agitation in an artificial gastric juice prepared by Gunnar Kjems ApS, Copenhagen, under the name of Revolyt. The constituents of the artificial gastric juice are as follows (per liter):

| | | |
|---|---|---|
| Sodium | 67 mEq | (1.54 g) |
| Potassium | 15 mEq | (0.59 g) |
| Magnesium | 6 mEq | (72 mg) |
| Chloride | 60 mEq | (2.04 g) |
| Citrate | 22 mEq | (1.39 g) |
| Sulphate | 6 mEq | (0.29 g) |
| Glucose | 152 mmol | (30.0 g) |

Furthermore, specimens of the prosthesis were irradiated with $\beta$-radiation in doses of 50, 100 and 150 kGy. For each of the irradiation doses, the breaking strength was tested on a dry specimen and on a specimen immersed in Revolyt at 37° C. for 10 minutes.

The results obtained are shown in the table below:

TABLE

| | Unirradiated | | | | 50 kGy | |
|---|---|---|---|---|---|---|
| | Dry | 5* | 10* | 20* | Dry | 10* |
| Compressive strength (N) | 40 ± 4 | 20 | 11 | 2.4 | 51 ± 4.5 | 14 |
| Stiffness (N/mm) | 94 ± 15 | | | | 109 ± 15 | |
| Displacement at fracture (mm) | 0.46 ± 0.07 | | | | 0.6 ± 0.06 | |

| | 100 kGy | 150 kGy | |
|---|---|---|---|
| | 10* | Dry | 10* |
| Compressive strength (N) | 60 ± 8 5 | 12** | 79 ± 9 | 23 |
| Stiffness (N/mm) | ~110 | | 125 | |
| Displacement at fracture (mm) | 0.7 | | 0.8 ± 1.1 | |

*number of minutes in Revolyt at 37° C.
**only one measurement

It will be seen from the table that the compressive breaking strength of the prosthesis is lowered significantly when immersed into the artificial Revolyt gastric juice. Furthermore, it transpired that the irradiation with $\beta$-particles, due to radiation-induced cross-linking, increased significantly as a result of the radiation treatment. However, it was found that a radiation dose of 50 kGy was sufficient to ensure sterility.

Specimens of the prosthesis were also used for test anastomosis of the small intestine on live pigs. The surgeons carrying out the operations reported that the prosthesis first of all facilitated keeping the two organ halves in a proper relation to one another due to the sticky properties of the polyethylene glycol following contact with the mucous membrane. Furthermore, it was reported that the prosthesis facilitated placing the interrupted stitches with even distances to one another, in particular in the region around the mesenterium where access is often difficult. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A prosthesis for use in joining hollow organ parts or systems, said prosthesis comprising a fragmentable body defining outer organ-supporting surface parts thereon adapted to be arranged in abutting relationship with inner surface parts of the organs to be joined;

said body having a compressive strength sufficiently low to allow fragmentation of the body by application of a pressure to the outer surface of the tubular organs subsequently to the anastomosing of the same, said pressure being below a pressure causing any substantial lesion of the tissue of the tubular organ parts and said compressive strength being in the range of from 20 to 100N.

2. A prosthesis according to claim 1 wherein said polyglycol material is polyethylene glycol which has an average molecular weight in the range of from 10,000 to 35,000.

3. A prosthesis according to claim 1 wherein said body has a substantially circular cross-section.

4. A prosthesis according to claim 1 wherein the ratio between the length and the largest diameter of the prosthesis is in the range form 2:1 to 7:1.

5. A prosthesis according to claim 1 wherein said body comprises end portions the supporting surface parts and a narrowed intermediate portion therebetween.

6. A prosthesis according to claim 1 wherein said body comprises end portions with tapered outer ends.

7. A prosthesis according to claim 1 wherein said body defines an inner cavity.

8. A prosthesis according to claim 7 having closed ends.

9. A prosthesis according to claim 7 having open ends.

10. A prosthesis according to claim 1, wherein said body is comprised of a degradable, non-toxic material that is solid at a temperature of at least 40° C.

11. A method for joining hollow organ parts or system, said method comprising
   1) inserting a prosthesis according to claim 1 into and between the organs to be joined;
   2) joining the two organ parts by anastomosis; and
   3) fragmenting the prosthesis by application of pressure to the outer surface of the tubular organs.

12. A prosthesis according to claim 11, wherein said material is solid at a temperature of at least 50° C.

13. A prosthesis according to claim 11, wherein said material is solid at a temperature of at least 60° C.

14. A prosthesis according to claim 2, wherein said polyethylene glycol has an average molecular weight in the range of from 15,000 to 30,000.

15. A prosthesis according to claim 1, wherein said compressive strength is in the range of from 30 to 80N.

16. A prosthesis according to claim 15, wherein said compressive strength is in the range of rom 40 to 70N.

17. A prosthesis according to claim 16, wherein said compressive strength is in the range of from 50 to 60N.

18. The method according to claim 11, wherein said pressure is less than the minimum pressure needed to cause any substantial lesion of the tissue of the tubular organ parts.

19. A prosthesis according to claim 1 which further comprises at least one thread-like fixation means having one end connected to the intermediate portion of the body for temporarily fixing the organ parts to the prosthesis.

20. A prosthesis according to claim 19, wherein said material is selected from the group consisting of hard paraffin, beeswax, ceresin, higher fatty alcohols, cholesterol, japan wax, kokkum butter, lard, microcrystalline wax, fractionated palm kernel oil, spermaceti, cetyl esters wax, squalene, wool alcohols, wool fat, carnauba wax, polyglycols, theobroma oil, chocolate, macrogol ethers, glycerol ethers, glycol ethers, and poloxamers.

21. A prosthesis according to claim 20, wherein said material is a polyglycol.

22. A prosthesis according to claim 14, wherein said polyethylene glycol has an average molecular weight of about 20,000.

* * * * *

UNITED STATES PATENT AND TRADEMARK OFFICE
CERTIFICATE OF CORRECTION

PATENT NO. : 5,180,392
DATED : January 19, 1993
INVENTOR(S) : Einar Skeil and Daniel Bar-shalom It is certified that error appears in the above-identified patent and that said Letters Patent is hereby corrected as shown below:

Column 12:

In claims 12 and 13, line 1, change "claim 11" to

-- claim 10 --.

Signed and Sealed this

Twenty-first Day of December, 1993

Attest:

BRUCE LEHMAN

*Attesting Officer*   *Commissioner of Patents and Trademarks*